United States Patent [19]

Hannay et al.

[11] Patent Number: 5,350,691
[45] Date of Patent: * Sep. 27, 1994

[54] METHOD FOR ABANDONING AN UNDERGROUND STORAGE TANK

[76] Inventors: Richard C. Hannay, 11807 S. Red Cedar Cir., The Woodlands, Tex. 77380; Dudley B. Pate, 4406 Ingersoll, Houston, Tex. 77027

[*] Notice: The portion of the term of this patent subsequent to Aug. 24, 2010 has been disclaimed.

[21] Appl. No.: 75,326

[22] Filed: Jun. 11, 1993

Related U.S. Application Data

[63] Continuation-in-part of Ser. No. 749,678, Aug. 26, 1991, Pat. No. 5,238,842.

[51] Int. Cl.$^5$ ............... E02D 5/00; A62D 3/00; C12S 9/00; C12S 13/00; B09B 3/00
[52] U.S. Cl. .................. 435/262.5; 435/262; 435/264; 405/272; 588/252
[58] Field of Search ............ 435/262, 262.5, 264; 405/272; 588/252

[56] References Cited

U.S. PATENT DOCUMENTS 5,238,842  8/1983  Hannay et al. ............ 435/262.5

*Primary Examiner*—Michael G. Wityshyn
*Assistant Examiner*—T. J. Reardon
*Attorney, Agent, or Firm*—Bill B. Berryhill

[57] ABSTRACT

A method of abandoning an underground storage tank including the steps of: removing residuals, if any, from the tank and filling the tank with a mixture which includes water, sand, a binding agent and a material for promoting uniform mixing of said mixture. In one embodiment of the invention, a surfactant is added to reduce the amount of water required by the mixture.

15 Claims, No Drawings

METHOD FOR ABANDONING AN UNDERGROUND STORAGE TANK

CROSS-REFERENCE TO RELATED APPLICATION

The present application is a continuation-in-part of corresponding application Ser. No. 07/749,678, filed Aug. 26, 1991, now U.S. Pat. No. 5,238,842.

BACKGROUND OF THE INVENTION

1. Field of the Invention

The present invention pertains to methods and procedures for abandoning underground storage tanks, particularly those which contain or have contained hydrocarbon substances or any other substances of an environmentally hazardous nature.

2. Description of the Prior Art

There are thousands and probably millions of underground storage tanks in which gasoline, fuel oil or other hydrocarbons have been stored. The Environmental Protection Agency indicates that it is aware of at least five million underground fuel tanks in the United States of which an estimated thirty percent leak. Even though large numbers of these tanks may have been abandoned, many of them leak or have leaked residual substances into the surrounding soil. Others may not have yet leaked but will do so in the future. All of such underground storage tanks are potential pollution problems, polluting the surrounding soil and possible water sources. Federal and state agencies are now requiring that these tanks be removed or cleaned up and abandoned in some environmentally safe method.

Abandoned underground storage tanks also create many other related problems. Due to the potential liability from environmental pollution, the owners of property on which underground storage tanks may be situated are frequently prevented from transfer or sale of the property for several reasons. First and foremost, potential buyers do not want to assume the risk associated with abandoned underground storage tanks. Secondly, banks and other lending institutions may not be willing to loan money to the owner or purchaser of businesses, such as service stations, garages, etc., where underground storage tanks are involved. Some court decisions have held lenders liable for cleanup costs if they had foreclosed on contaminated property or had merely advised businesses that owned contaminated land. Lending institutions are thus reluctant to expose themselves to such potentially costly problems.

Because of the risks associated with underground storage tanks, new measures are being taken in new installations for detecting and preventing leaking underground storage. In some cases tanks are being placed above ground. However, this does not solve the problem of leaking tanks already in place.

The abandonment of subterranean cavities, such as abandoned mines, has long been of concern. U.S. Pat. No. 1,404,112 discloses a method of filling a subterranean cavity in which a slurry of soil and water is pumped into the cavity behind a temporary wall. The water is allowed to leak through the temporary wall, the soil remaining in position within the cavity. U.S. Pat. No. 3,892,442 discloses a more recent mining approach to this problem in which a foam material is dispensed in a mining shaft to fill the void created by removal of the mined product. Materials mentioned are polystyrene, polyurethane, foam cement, foam plastic, etc. Appropriate additives make the foam fire retardant.

The most widely utilized and accepted method of abandoning underground storage tanks at the present time is removal of the tanks. However, this is a very expensive, time consuming and business interrupting procedure. If any residual fluids are in the tank, they must be pumped out and disposed of in an acceptable manner. Heavy equipment must be brought in to remove soil surrounding the tank and the tank itself. If the surrounding soil is contaminated, the contaminated soil must be removed, temporarily contained and eventually disposed of in a manner acceptable to environmental pollution agencies. While waiting for disposal, the contaminated soil, due to vaporization of the contaminating substances therein, may pose health problems to the surrounding area. Then the cavity resulting from removal of the tank and/or the surrounding soil must be filled with uncontaminated soil. Such an operation may require days or even weeks and may be very destructive to other improvements of the subject property such as driveways, sidewalks, etc. It is most likely that such operations will also disrupt or totally suspend business operations of the business on whose property the tanks are disposed. It can be seen that this creates major problems.

Of course, the costly and disruptive procedure of removing an abandoned underground storage tank could be avoided if an acceptable method were found to abandon these tanks in place. One such method is proposed in U.S. Pat. No. 4,693,284 in which an abandoned underground storage tank is filled with a rigid polyurethane foam. The method revealed therein suggests removing any residual substances and evacuation and/or evaporation of vapors therefrom by forced air ventilation. It is suggested that prior to filling the tank with foam, minor amounts of solid absorbent materials be place in the tank to absorb condensation, water, mud, or sludge that might be left in the tank. It is not known whether this procedure has been approved by the various environmental pollution agencies. It is suggested in the patent that it might become necessary in the future to remove the tank as a result of regulatory requirements and that if the tank is removed it would be easier to handle filled with foam than not. Even if this procedure is approved and the tank never removed from the ground, a large mass of plastic foam is left in place, rendering a certain area of the property less usable for things such as structural support, water drainage, certain types of landscaping, etc. For example, the compressive strength of polyurethane is approximately 30 psi, substantially less than soil which is usually around 45 psi. Furthermore, filling a tank with polyurethane foam is relatively expensive and would be subject to exothermic reactions of 200 degrees F. or more, creating potential explosion hazards.

On the other hand, if the tank is filled with cement, the compressive strength is usually not less than 1500 psi. This creates a problem if, for any reason, future activities require digging a hole or trench through the tank fill material. Furthermore, it is almost impossible to completely fill a tank with cement since the cement does not flow easily into the tank.

As can be understood, the abandonment of underground storage tanks, particularly those in which hydrocarbon materials or their hazardous substances have been stored, has become a major problem. Efforts continue to be made to solve this problem in a safe, cost effective and environmentally accepted manner. Further improvements are needed.

SUMMARY OF THE PRESENT INVENTION

The present invention provides a new method of abandoning an underground storage tank which includes the steps of: removing residual substances, if any, from the tank; washing the tank with a detergent solution; and filling the tank with a mixture which includes water, sand, a binding agent and a material for promoting a uniform mixture and retarding separation of the components thereof. If there is any piping connected to the tank, it may be filled with expanding plastic foam prior to filling of the tank with the mixture. The method may also include steps which include hydrocarbon bio-remediation and accelerated decomposition of the tank.

Thus, the present invention provides a method of abandoning an underground storage tank which, most importantly, should be acceptable to regulatory agencies. It provides a method by which an underground storage tank may be abandoned in place, eliminating the costly and business interruptive methods which require removal of the tank. When the method is completed, the tank is filled with materials which provide enough structural support and should not interfere with future use of the land as might be the case with other methods. In fact, in some embodiments of the invention, the surrounding tank may eventually be totally decomposed.

All operations of the method of the present invention may be conducted through the fill connections of an underground storage tank, avoiding potentially hazardous operations and major construction activity such as removal and installation of drives and parking areas. In most cases, the procedure can be conducted in a short period of time and at any time of the day, resulting in minimum interruption of business activities at the site.

Since requirements of environmental pollution agencies are met and since the procedure is effective and much less costly than other procedures, many of the problems associated with use and/or sale of the property are eliminated. This method should greatly reduce lending institutions reluctance to lend money to the owners or users of property on which underground storage tanks are located. Many other objects and advantages of the invention will be seen from the description which follows.

DESCRIPTION OF PREFERRED EMBODIMENT

Prior to taking active steps to abandon an underground tank, the soil surrounding the tank should be tested for contamination by former tank contents, particularly governmentally regulated substances. The size of the tank and the size and length of piping connected thereto should be determined. If there are any residual substances in the tank, the nature of these substances should be determined, if possible, and they should be removed by a vacuum truck, or the like, for proper disposal.

Then the tank is preferably washed with a solution of water, a surface tension reducing surfactant (detergent) and hydrocarbon devouring microbes. This is preferably done by placing spray nozzles in the tank through the fill connection of the tank. The hydrocarbon devouring microbes, through a process referred to as bio-remediation, breaks down any hydrocarbons remaining in the tank into acceptable products of fatty acids and carbon dioxide. For this to take place, the washing solution is preferably left in the tank for several days (fifteen to thirty days). After the tank is sufficiently washed and bio-remediation has taken place, the washing solution and materials washed thereby may be removed for disposal. In some cases, it may be left in the tank to mix with the fill mixture.

At this point, any piping connected to the tank should be filled. Before filling the piping, any residual materials therein should have been removed. The piping is preferably filled with an expanding plastic foam or the like. A suitable mixture for producing expanding urethane foam compatible with tank residue would be an isocyanate compound and polyhydric alcohol. These components are simply mixed together in a suitable ratio, e.g. one to one by volume, to produce expanding urethane foam. Since the size and length of the piping has been previously determined, the amount of foam materials necessary for filling the volume of the piping is introduced in the piping at some distance from the tank and forced toward the tank by the expanding foam. It usually takes anywhere from thirty seconds to two minutes for the foam to expand and fill the piping with an inert material. This material may typically have a ten or twenty to one expansion rate. The ends of the piping are then capped.

Then the tank is filled with a mixture which includes water, sand, a binding agent and a material for promoting uniform mixing and retarding separation of components of the mixture. A typical composition for the mixture, in percentage by volume would be:

| Material | Volume by % |
| --- | --- |
| Sand | 55.0 |
| Water | 22.3 |
| Fly Ash | 18.0 |
| Sodium Silicate | 3.7 |
| Triacetin | 0.3 |
| Metal Salts | 0.7 |

Of course, the percentage may vary. The compressive strength of this mixture, after hardening, would be around 40 to 100 psi.

With a mixture such as described above, a certain amount of excess water is present. As the tank is filled, excess water flows out of the tank and must be disposed of. This also results in increased time to fill the tank. It has been found that if a surfactant from a group of fatty acid alkyl amide surfactants is added to the mixture, the amount of water needed is substantially reduced and excess water does not flow from the tank. This requires substantially less time to fill the tank. Furthermore, the ratio of sand to other components is substantially increased, resulting in less cost for other components. With a surfactant 0.005 to 0.009% by volume, a typical composition for the mixture would be:

| Material | Volume by % |
| --- | --- |
| Sand | 81.0 |
| Water | 6.4 |
| Fly Ash | 10.25 |
| Sodium Silicate | 1.5 |
| Triacetin | 0.15 |
| Metal Salts | 0.7 |

The compressive strength of this mixture, after hardening, would be approximately 250 psi, slightly more than soil but substantially less than concrete.

Fly ash is included in the mixture to promote uniform mixing of the mixture and to retard separation of its components as it is being introduced into the tank. Other materials may be used for this purpose. Other materials suitable for this purpose are fumed silica, attapulgite clay, dry flow starch, kiln dust, etc.

Sodium silicate is the material which binds the materials of the mixture together as it sets up. Triacetin is a catalyst for the binder. Another catalyst which would decrease the reaction time is muriatic acid. Other catalysts are citric acid and sodium flow silicate (sodium silica fluoride).

Metal salts may be included in the mixture to provide an electrolyte to enhance corrosion and eventual decomposition of the metal tank. Thus, the metal salts used should be those metals which are more noble than ferrous.

Of course, the greatest advantage of the procedure of the present invention is the abandonment of an underground storage tank without having to remove the tank from the ground. The complete procedure may be completed within a few hours and may be done after normal business hours. Thus, interruption of business and business facilities is reduced to a minimum. The abandoned tank is left filled with a solid, basically inert material which is capable of supporting structural loads much as the surrounding soil. This procedure should alleviate many of the problems associated with the sale and lending of money on projects associated with the property.

The method of the present invention has been described in its preferred form. However, it should be understood that this method and the steps thereof can be varied considerably without departing from the spirit of the invention. Accordingly, it is intended that the scope of the invention be limited only by the claims which follow.

We claim:

1. A method of abandoning an underground storage tank in which hydrocarbon substances have been stored comprising the steps of:
   a. removing residual substances, if any, from said tank; and
   b. completely filling said tank with a mixture which includes water, sand, a binding agent and a material for promoting uniform mixing of said mixture wherein said mixture forms a solid composition with a structural strength of 40 psi to 250 psi.

2. The method of claim 1 in which said mixture includes a fatty acid alkyl amide surfactant in an amount sufficient to reduce the amount of water required by said mixture.

3. The method of claim 1 in which said mixture includes a catalyst for said binding agent.

4. The method of claim 3 in which said catalyst is selected form the group consisting of: triacetin, muriatic acid, citric acid and sodium silica fluoride.

5. The method of claim 1 in which said material for promoting uniform mixing of said mixture is selected from the group consisting of: fly ash, fumed silica, attapulgite clay, dry flow starch and kiln dust.

6. The method of claim 1 in which said mixture includes by volume 6% to 23% liquids and 77% to 94% solids.

7. The method of claim 6 in which said mixture includes by volume approximately 55% to 81% sand.

8. The method of claim 7 in which said mixture includes by volume approximately 6% to 22% water.

9. The method of claim 6 in which said material for promoting uniform mixing of said mixture makes up by volume approximately 10% to 18% of said mixture.

10. The method of claim 1 in which said mixture includes a surfactant and the approximate percentages, by volume, of the following materials: 81% sand, 6.4% water, 10.25% fly ash, 1.5% sodium silicate, 0.15% triacetin.

11. The method of claim 10 in which said mixture also includes by volume approximately 0.7% metal salts.

12. The method of claim 1 wherein the step of removing the residual substances includes the step of introducing hydrocarbon devouring microbes into said tank for bio-remediation of any residual hydrocarbon substance in said tank prior to filling of said tank with said mixture.

13. The method of claim 12 in which said hydrocarbon devouring microbes are allowed to reside in said tank for several days prior to said filling of said tank with said mixture.

14. The method of claim 1 including the steps of washing said tank with a detergent solution and removing said detergent solution from said tank prior to filling said tank with said mixture.

15. The method of claim 1 in which said storage tank is made of ferrous material, said mixture including metal salts more noble than said ferrous material to enhance the corrosion of said storage tank.

* * * * *